(12) United States Patent
Berger et al.

(10) Patent No.: US 10,664,985 B2
(45) Date of Patent: May 26, 2020

(54) DETERMINING A COMPLEXITY VALUE OF A STENOSIS OR A SECTION OF A VESSEL

(71) Applicants: Martin Berger, Erlangen (DE); Thomas Redel, Poxdorf (DE)

(72) Inventors: Martin Berger, Erlangen (DE); Thomas Redel, Poxdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 203 days.

(21) Appl. No.: 15/881,187

(22) Filed: Jan. 26, 2018

(65) Prior Publication Data

US 2018/0218514 A1 Aug. 2, 2018

(30) Foreign Application Priority Data

Jan. 27, 2017 (EP) ..................................... 17153565

(51) Int. Cl.
*G06K 9/00* (2006.01)
*G06T 7/60* (2017.01)
(Continued)

(52) U.S. Cl.
CPC ............ *G06T 7/60* (2013.01); *A61B 5/02007* (2013.01); *G06T 7/0012* (2013.01);
(Continued)

(58) Field of Classification Search
CPC ....... G06T 7/60; G06T 7/0012; G06T 11/008; G06T 2207/10116; G06T 2207/30172; G06T 2207/20224; G06T 2207/10081; G06T 2207/30101; G06T 2207/30048; G06T 2207/20081; A61B 5/02007; A61B 5/7257; A61B 5/7264; A61B 2576/00; A61B 5/726; A61B 5/026; A61B 5/7236;
(Continued)

(56) References Cited

U.S. PATENT DOCUMENTS

2012/0236259 A1* 9/2012 Abramoff ................ A61B 3/12
351/206
2014/0003701 A1* 1/2014 Masood ................ G06T 7/0012
382/134

(Continued)

OTHER PUBLICATIONS

European Search Report for related European Application No. 17153565.1 dated Apr. 21, 2017.
(Continued)

*Primary Examiner* — Van D Huynh
(74) *Attorney, Agent, or Firm* — Lempia Summerfield Katz LLC

(57) ABSTRACT

Systems and methods are provided for evaluating the complexity of a stenosis or a section of a vessel. At least one image of the stenosis or the section of the vessel is provided. A geometrical feature value of the stenosis and/or or the section of the vessel is identified from the at least one image. At least one intensity feature value is determined based on a grey level intensity of the stenosis or the section of the vessel from the at least one image. A complexity value relating to the geometrical complexity of the stenosis or the section of the vessel is calculated as a function of the at least one geometrical feature value and the at least one intensity feature value of the stenosis or the section of the vessel.

20 Claims, 2 Drawing Sheets

(51) Int. Cl.
| | |
|---|---|
| *A61B 5/02* | (2006.01) |
| *G06T 7/00* | (2017.01) |
| *G06T 11/00* | (2006.01) |
| *A61B 6/00* | (2006.01) |
| *A61B 5/055* | (2006.01) |
| *A61B 5/00* | (2006.01) |
| *A61B 5/026* | (2006.01) |

(52) U.S. Cl.
CPC ............ *G06T 11/008* (2013.01); *A61B 5/026* (2013.01); *A61B 5/055* (2013.01); *A61B 5/726* (2013.01); *A61B 5/7239* (2013.01); *A61B 5/7257* (2013.01); *A61B 5/7264* (2013.01); *A61B 6/481* (2013.01); *A61B 6/504* (2013.01); *A61B 6/507* (2013.01); *A61B 6/5217* (2013.01); *A61B 2576/00* (2013.01); *G06T 2207/10081* (2013.01); *G06T 2207/10116* (2013.01); *G06T 2207/20081* (2013.01); *G06T 2207/20224* (2013.01); *G06T 2207/30048* (2013.01); *G06T 2207/30101* (2013.01); *G06T 2207/30172* (2013.01)

(58) Field of Classification Search
CPC ....... A61B 6/5217; A61B 6/507; A61B 6/481; A61B 5/055; A61B 6/504
USPC ........................................................ 382/130
See application file for complete search history.

(56) References Cited

U.S. PATENT DOCUMENTS

| | | | |
|---|---|---|---|
| 2014/0029816 A1* | 1/2014 | Graham | G06T 7/0012 382/131 |
| 2014/0073976 A1* | 3/2014 | Fonte | G06N 7/005 600/504 |
| 2014/0378850 A1* | 12/2014 | Plakas | A61B 5/026 600/504 |
| 2015/0066818 A1* | 3/2015 | Choi | A61B 5/02007 706/12 |
| 2015/0254850 A1* | 9/2015 | Jorgensen | G06T 7/0016 382/133 |

OTHER PUBLICATIONS

Itu, Lucian et. al.: "A Machine Learning Approach for Computation of Fractional Flow—Reserve from Coronary Computed Tomography"; in: J Appl Physiol; 2016; DOI 10.1152/japplphysiol.00752. 2015.

Wei, Jun et al.: "Computerized detection of noncalcified plaques in coronary CT angiography: Evaluation of topological soft gradient prescreening method and luminal analysis"; in: Med. Phys.; vol. 41, No. 8; pp. 081901-1-081901-9; 2014; XP 012187736; ISSN 0094-2405.

Syngo Workplace—Angio/Quant, Operator Manual, Siemens AG, Medical Solutions, Angiography & Interventional X-Ray Systems, Siemensstr. 1, 91301 Forchheim, www.siemens.com/healthcare, Apr. 2011, pp. 143-189.

* cited by examiner

DETERMINING A COMPLEXITY VALUE OF A STENOSIS OR A SECTION OF A VESSEL

CROSS REFERENCE TO RELATED APPLICATION

This application claims the benefit of EP 17153565, filed on Jan. 27, 2017, which is hereby incorporated by reference in its entirety FIELD Embodiments relate to a system and method of evaluating a geometrical complexity of a stenosis or a section of a vessel and a corresponding device for evaluating such geometrical complexity.

BACKGROUND

Stents may be used for treating coronary arteries that are constricted by plaque to re-establish the blood flow and thus the supply of the cardiac muscle.

A 3D-reconstruction of a blood vessel model may be used for estimating the degree of stenosis as well as for planning a treatment strategy. A 3D-blood-vessel model is developed based on at least two angiographic scenes. The precision of the reconstructed blood vessel model is decisive, since the precision directly affects the evaluation of the stenosis or the section of the vessel. "Stenosis" refers to both a stenosis and a section of a vessel.

Due to the limited number of angiographic pictures, the geometric complexity of the 3D-models may be restricted to elliptical cross-sections that are located on a reconstructed 3D-center-line. The re-construction of the models is based on 2D-segmentations of a vessel contour and the vessel center line. The effects of stenoses on the 2D-contour of the vessel strongly depends on the complexity of the stenoses, but also on the perspective of the single views.

FIGS. 1 to 4 illustrate the problem. A metal phantom is used to model an axisymmetric stenosis 1 and an eccentric stenosis 2. Projection images show significant differences of the contours of both stenosis 1 and 2.

FIGS. 1 to 4 depict, for example, different LAO (left anterior oblique) views. FIG. 1 is a view at LAO=90°, FIG. 2 a view at LAO=60°, FIG. 3 a view at LAO=30° and FIG. 4 a view at LAO=0°. The geometrical contour of the axisymmetric stenosis 1 is equally formed in each of the views of FIGS. 1 to 4. However, the contour of the eccentric stenosis 2 may only be seen in the views of FIGS. 1 and 2, e.g. only the views at LAO=90° and LAO=60° depict a crescent shape at the edge of the vessel 3 (represented by the metal phantom). Since the eccentric stenosis does not cover the complete circumference of the vessel, the eccentric stenosis is almost completely hidden in unfavorable views like LAO=0° and LAO=30° (compare FIGS. 3 and 4). The views do not allow a contour based reconstruction of the eccentric stenosis 2.

One solution of the problem is to take additional pictures at further angles that provide important information for improving the 3D-model. Such additional pictures, however, have the disadvantage that the additional pictures increase the time and consequently the costs for acquisition and processing of the pictures. Additionally, the dose of radiation increases for the patient and the cardiologist. Therefore, additional pictures may only be taken if the complexity of the stenosis requires the additional pictures.

If the stenosis is diagnosed directly from 2D-angiography data, the number of pictures and corresponding views are manually assessed by the physician. Furthermore, there is no automated solution for the evaluation of the complexity and the reconstructability of the stenosis based on the 2D-angiography data.

The article of Itu, Lucian, et al.: "A Machine Learning Approach for Computation of Fractional Flow Reserve from Coronary Computed Tomography", Journal of Applied Physiology, Apr. 14, 2016, presents a machine learning based model for predicting FFR (fractural flow reserve) as an alternative physician-based approach. The model is trained on a large database of synthetically generated coronary anatomies, where the target values are computed using the physician-based model. The trained model predicts FFR at each point along the center line of the coronary tree and its performance was assessed by comparing the predictions against physician-based computations.

SUMMARY AND DESCRIPTION

Embodiments provide a method of evaluating a geometrical complexity of a stenosis that is used as a basis for deciding whether further images of the stenosis are to be acquired for performing a 3D-econstruction of the stenosis.

The scope of the present invention is defined solely by the appended claims and is not affected to any degree by the statements within this summary. The present embodiments may obviate one or more of the drawbacks or limitations in the related art.

A method is provided for evaluating a geometrical complexity of a stenosis or a section of a vessel by providing at least one image/picture of the stenosis or the section of the vessel, gathering at least one geometrical feature value of the stenosis from the at least one image, gathering at least one intensity feature value based on an optical intensity of the stenosis or the section of the vessel from the at least one image and automatically determining a complexity value related to the geometrical complexity of the stenosis or the section of the vessel in dependency on the at least one geometrical feature value and the at least one intensity feature value of the stenosis or the section of the vessel. The geometrical complexity relates to the geometrical form of the stenosis or the section of the vessel. The more complex a stenosis or vessel is, the more images of the stenosis or vessel may be necessary to reconstruct the stenosis or vessel with high quality in three dimensions. For the method, at least one image of the stenosis or the section of the vessel is used as starting point. At least one geometrical feature value is obtained from the image. The geometrical feature value may be a value representing the diameter, the length or any other geometrical parameter of the stenosis or the section of the vessel. For higher performance a plurality of geometrical feature values may be gathered. Individual complexity values may be gathered along the centerline of vessel.

Additionally, at least one intensity feature value is obtained or determined from the image. The intensity feature value relates to a grey level intensity of a region of the image that depicts the stenosis. The intensity reflects, for example, the attenuation of the (X-)rays for obtaining the picture or image.

The process of extracting geometrical or intensity-based features may also include one or multiple preprocessing steps on the projection image. For example, a vesselness filter or other gradient-based method may be applied to enhance the vessel structures and suppress the background anatomy.

In an embodiment multiple features may be combined to determine a complexity value µ. An alternative geometrical contribution may be provided by a comparison of the two outlines of the stenosis. The amount of correlated curvature k1 and k2 of both outlines from both side of the vessel segment containing the stenosis may be compared normalized by calculating a ratio or difference or more complex coefficients, for example:

$$\mu K = k1 - k2; \text{ or } K = k1 \times k2$$

The complexity value related to the geometrical complexity of the stenosis is determined automatically. No physician is needed to assess the complexity of the form of the stenosis, rather an automatic algorithm is used to determine the complexity of the geometrical form of the stenosis. The algorithm uses the at least one geometrical feature value and the at least one intensity feature value of the stenosis as input values. In one configuration there are only two different values to determine the complexity value, e.g. one geometrical feature value and one intensity feature value. In high-end configurations there may be used a plurality of geometrical feature values and a plurality of intensity feature values as a vector for automatically determining the complexity value.

Two different types of feature values are employed for evaluating the geometrical complexity of the stenosis. Additionally, plural subtypes of the feature types may be used for determining or estimating the complexity. A big parameter room may be utilized to obtain a simple but significant complexity value for the stenosis.

In one embodiment the at least one image may be provided by angiography. Other imaging techniques may be used for gathering the at least one image. For example, X-ray techniques or magnet resonance tomography may be used to obtain the images/pictures.

The at least one geometrical feature value may relate to one of a 2D-contour, a center line of a blood vessel or a curvature of a blood vessel. The 2D-contour may be obtained by an edge filter applied to the image. The 2D-contour may reflect the form of the stenosis. Alternatively, the geometrical feature value may relate to the center line of a blood vessel. For example, the distance of the stenosis from the center line may be of interest. The distance may vary along the center line. As a further geometrical feature, the curvature of the blood vessel may be of importance. The feature value may relate to the radius of curvature of the blood vessel. Other geometrical feature values like diameter, length, etc. may be used for determining the complexity of the stenosis or the vessel along its centerline, for example. Additionally, further processing functions like derivation, Fourier transformation, wavelet analysis etc. may be used for determining the complexity value. Position information of the centerline of the vessel or the lumen may also contribute to the complexity value.

Alternatively, the geometrical feature value may relate to the center line of a blood vessel. For example, the distance of the stenosis from the center line may be of interest. The distance may vary along the center line. As a further geometrical feature, the curvature of the blood vessel may be of importance. The feature value may relate to the radius of curvature of the blood vessel. Other geometrical feature values like diameter, length, etc. may be used for determining the complexity of the stenosis.

The at least one intensity feature value for determining the complexity of the stenosis may result from an attenuation or excitation of radiation and may relate to a sum, a distribution or an energy of gray values within one or more regions of the blood vessel. For example, the attenuation of radiation may be of interest when performing an X-ray screening. Alternatively, the excitation of radiation is used in MRT-screenings. Both the local attenuation and local excitation of radiation may lead to locally different gray values of an image. The gray values may be further processed to obtain one or more intensity feature values.

The complexity value of the stenosis may be determined by regression or classification of the at least one geometrical feature value and the at least one intensity feature value. Two or more values are provided as input values for a regression or classification algorithm to obtain the complexity value. Any type of regression algorithm and/or classification algorithm may be implemented. The complexity of the stenosis may be described with one single value. The complexity may also be defined by a plurality of values. The one or more complexity values may be provided for one position or plural positions along a centerline, for example.

Two, three or more values of one or more geometrical features and one or more intensity features may be gathered and the complexity value is determined by rating the feature values. For example, there is formed a vector of two, three or more values. Each value relates to a geometrical feature or an intensity feature. The vector includes at least one geometrical feature value and at least one intensity feature value. For determining the complexity value of the stenosis each value of the vector is rated. The rating of the plural values represents a type of regression.

The geometrical area may be estimated by the local diameter measured while the intensity might be estimated by using Beers law with the healthy segment used as reference for calibration. The area information may be used to derive symmetric r or hydraulic radii R for comparison. There are different ways to define complexity $\mu$. In one approach, the difference or ratio of the diameters at the maximum stenosis is measured on geometrical Ageo(stenosis) and intensity Aint (stenosis) based measurement. Complexity might for example be determined as:

$$\mu = A\text{geo}/A\text{int}; \text{ or } \mu = A\text{geo} - A\text{int}; \text{ or } \mu = (A\text{geo} - A\text{int})/A\text{geo}$$

or $$\mu = R\text{geo}/R\text{int}; \text{ or } \mu = R\text{geo} - R\text{int}; \text{ or } \mu = (R\text{geo} - R\text{int})/R\text{geo}$$

or $$\mu = r\text{geo}/r\text{int}; \text{ or } \mu = r\text{geo} - r\text{int}; \text{ or } \mu = (r\text{geo} - r\text{int})/r\text{geo}$$

Complexity $\mu$ may be determined at multiple locations A(x) along a stenosis with length 1. Based on the multiple numbers, an average, integrated, median, added, multiplied or a combination, single value may be obtained in the geometrical space as well as in the intensity based space. Alternatively, instead of multiple locations complete areas may be used. Complexity $\mu$ using multiple locations may for example be determined as:

$$\mu tot = \int_0^l \mu(x)dx; \text{ or}$$

$$\mu tot = \mu(1) \times \mu(2) \times \mu(3) \ldots ; \text{ or}$$

$$\mu tot = \text{median}(\mu(x)); \text{ or}$$

$$\mu tot = \Sigma \frac{A\text{geo}(x) \cdot dx}{A\text{int}(x) \cdot dx}$$

Further geometrical features may be the centerlines, or the curvature c of the centerline, calculated as measured geometrical feature or derived from the maximum of the intensity based distribution. In the latter case the location of the centerline in a cross section is defined by the maximum intensity along the cross section. Different mathematical operations are possible to compare both values to a complexity value µC, for example:

$$\mu = cgeo;\ or$$

$$\mu = cint\ \text{(geometrical or intensity based only);}$$

or combined $$\mu = cgeo - cint;\ \mu C = cgeo \times cint$$

The different features may be combined to generate an overall complexity measure:

$$\mu tot = \mu tot(A) \otimes \mu K \otimes \mu C \otimes \text{additional features}$$

with µtot(A)geometrical and intensity based, µK and µC intensity and/or geometrical based.

In a first image the analysis of the complexity µ is limited to the first image. After the second image the analysis may be performed in each of the available images. In addition, if there are an initial 3D reconstruction of the vessel segment with the stenosis both analyses are registered and may be analyzed in a combined way pointwise for each location of the stenotic segment and/or globally, for example:

$$\mu 3d = \mu image1 \otimes \mu image2$$

For example, a ratio of the at least one geometrical feature value and the at least one intensity feature value may be used for determining the complexity value. For example, a cross-sectional area of the vessel at the stenosis as geometrical feature value may be divided by a medium-gray level at the stenosis as intensity feature value in order to obtain the complexity value as quotient. The complexity value may be obtained very easily.

In an embodiment the automatically determining of the complexity value is performed using machine learning. For example, weights for rating the multiple feature values may be learned automatically. Alternatively, a classification algorithm may be learned automatically. High quality of the complexity value may be expected.

A large variety of possible features exist, e.g. geometrical or intensity features. Methods of machine learning provide a suitable framework to learn and extract stenotic complexity or reconstructability.

As input to the approach includes N known 3D volumetric data of contrast filled vessel segments or vessel trees. The data may be obtained by CTA, coronary MRI, or other coronary imaging modalities. Simulated vessel anatomies may be used. Additionally, N 3D surface models or volumetric segmentations of the vessels, corresponding to the known 3D volumes are obtained.

The vessel complexity or reconstructability is defined as single or multiple quantitative measures that may be directly extracted from the known 3D vessel data. The quantitative values are used as ground truth for training of the machine learning algorithm. Multiple such values may also be assigned as ground truth to particular locations within the known vessel segments or trees, e.g., along locations along the vessels' centerlines.

In the following a definition for extraction of a reconstructability measure is provided.

A large number of K simulated projection images are generated from of the known 3D volumetric vessel data. All possible combinations of M selected projection images are used as input for a given symbolic reconstruction algorithm (e.g., IZ3D), where M=1, 2, . . . , K. Every obtained symbolic 3D reconstruction is compared with respect to its similarity to the known 3D surface model or segmentation. The similarity measure is identical to the vessel complexity or reconstructability and may be given by:

1) The computation of a DICE score, that measures the overlap of the known 3D segmentation of the vessel and the binarized symbolic reconstruction. The DICE score evaluates to 1 if the segmentations are identical and to 0 if the segmentations do not overlap at all.
2) The Hausdorff distance, e.g. the distance between the known, 3D surface model and the reconstructed 3D surface model.
3) Any other similarity metric defined between the reconstructed symbolic 3D data and the known, 3D vessel data.
4) All measures may also be obtained locally, leading to a multitude of complexity or reconstructability values that may be assigned to specific vessel locations, e.g., along the centerline.

In addition to the symbolic 3D reconstruction, geometric and intensity features are extracted from the M selected 2D projection images. Geometric features may be represented but are not limited to the radius, curvature, length, cross section area, of the segmented vessel. Variations and combinations of such measures along the centerline, e.g., determined by the Fourier transformation, wavelet analysis, derivatives of different orders, integration, or multiplication, may also be employed. Intensity features may be represented but are not limited to the sum, distribution, moments of gray values within a region of the vessel, e.g. along a line orthogonal to the 2D centerline but within the vessel outline. M may represent a feature value.

Based on the ground truth reconstructability or complexity index, a machine learning regression or classifier may be trained, e.g., weights and combinations of features are determined.

In the actual application phase, the known 3D volumetric data is no longer necessary. The same features are extracted from an acquired or loaded angiographic image as obtained for the training phase. The machine learning algorithm applies its learned weights and combinations to the extracted features such that an estimate of the reconstructability or complexity index is computed. For example, the measure may be used to decide if the reconstruction quality will be sufficient or if it needs improvement, e.g. by an additional acquired view.

In one embodiment the stenosis is an eccentric stenosis. The stenosis may not be seen directly from all sides of the blood vessel. For an eccentric stenosis, the visible area of the stenosis changes with the angle of view whereas the intensity value of the stenosis region remains constant for different angles of view. With both values the complexity or the type of the stenosis may be determined.

The complexity value may be used to determine whether a 3D-reconstruction of the stenosis is possible or not. The complexity value characterizes the form or type of the stenosis. In an application, the complexity value is compared to a threshold. If the threshold is exceeded or fallen short a 3D-reconstruction may be not possible. A corresponding notice may be generated automatically.

The complexity value may be used to determine whether a further image of the stenosis is required. An automatic recommendation concerning the necessity of an additional image may be generated. The dose of radiation may be kept as small as possible for the patient.

Embodiments provide a device for evaluating a geometrical complexity of a stenosis including storage for providing at least one image of the stenosis, an analyzer for gathering at least one geometrical feature value of the stenosis and/or a region of the vessel at the stenosis from the at least one image and for gathering at least one intensity feature value based on a grey level intensity of the stenosis from the at least one image, a processor for automatically determining a complexity value related to the geometrical complexity of the stenosis in dependency on the at least one intensity feature value of the stenosis.

In an embodiment, the device is used in an angiography system.

DETAILED DESCRIPTION

Embodiments provide a combination of different features of the stenosis. The features originate from 2D-projection images of the blood vessel with the stenosis. The features relate to geometrical data and data based on intensity values of the image. Pure geometrical features (e.g., the contour of the blood vessel) strongly depend on the viewing direction and the form of the stenosis. However, the total absorption of the X-rays caused by the blood vessel predominantly does not depend on the viewing directions as described with reference to FIGS. 1 to 4. Though the eccentric stenosis 2 is no longer identifiable in its contour at LAO=0° and LAO=30°, the eccentric stenosis 2 is recognizable in the gray values.

Figure 1:
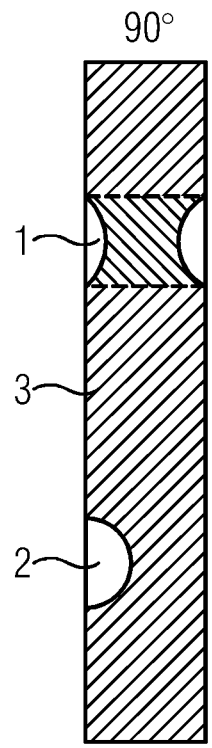
FIG. 1 depicts a simulation of an axisymmetric and an eccentric stenosis at a viewing angle of 90°.
Figure 2:
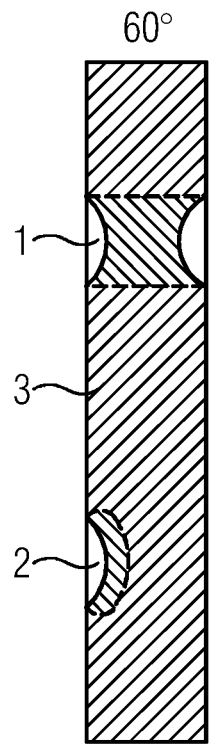
FIG. 2 depicts the two stenoses at a viewing angle of 60°.
Figure 3:
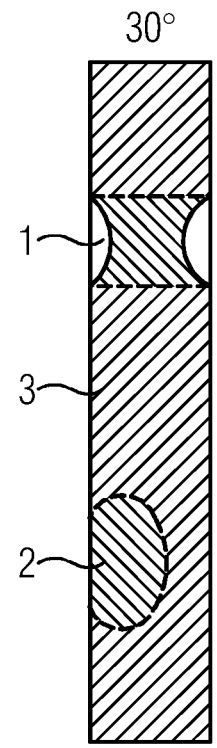
FIG. 3 depicts the two stenoses at a viewing angle of 30°.
Figure 4:
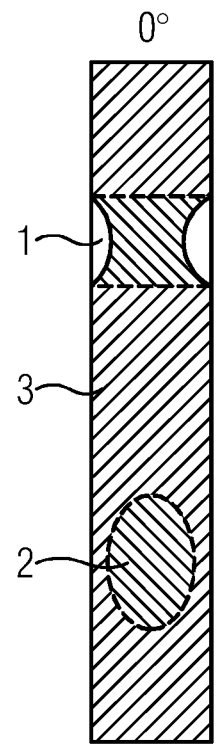
FIG. 4 depicts the two stenoses at a viewing angle of 0°.
Figure 5:
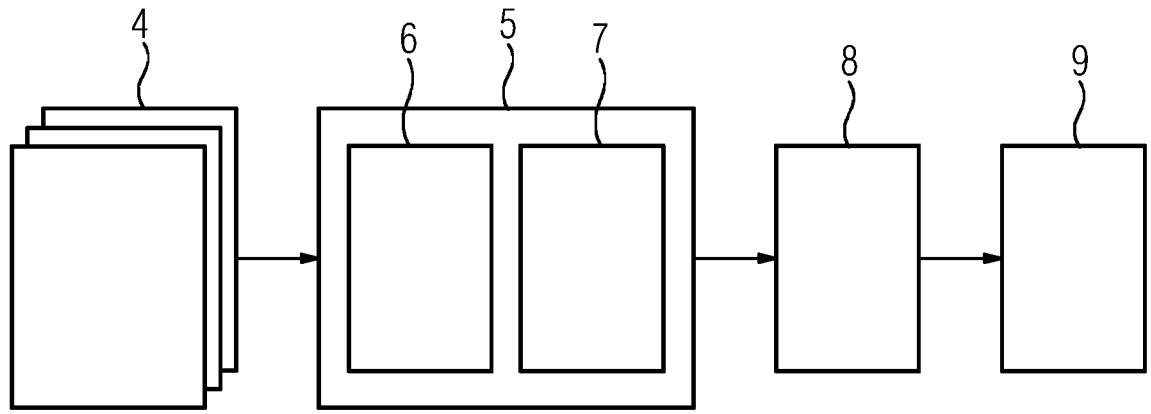
FIG. 5 depicts a diagram showing a method for evaluating the complexity of a stenosis according to an embodiment.

FIG. 5 depicts an embodiment of a method of evaluating the complexity of a stenosis. One or more angiographic images 4 are provided. A feature extraction 5 is performed on the angiographic images 4. An analyzer may be used for performing such feature extraction. The feature extraction 5 contains two different algorithms. A first algorithm 6 for extracting geometrical features or respective values. The first algorithm 6 may perform a segmentation of the objects in the images 4.

A second algorithm 7 of the feature extraction 5 may extract intensity features or respective values. For example, densitometry is performable with the second algorithm 7.

The features or feature values obtained from the algorithms 6 and 7 or the feature extraction 5 (e.g., the analyzer) may be input to the processor 8. The processor 8 may perform a regression or classification algorithm. The processor 8 outputs a complexity value 9 of the stenosis. The complexity value 9 may be further processed to provide a value related to the ability of reconstructing the stenosis (e.g., a value related to the decision: "stenosis sufficiently described for reconstruction?"). The value represents the corresponding decision "yes"/"no".

Geometrical features extracted by algorithm 6 may relate to the 2D-contour, the center line or the curvature of the segmented blood vessel. For example, an edge detector is used for extracting the edges of the blood vessel or the stenosis to obtain the respective contour or other features of the vessel.

Intensity features or intensity feature values, respectively, are calculated as a function of, for example, the attenuation of X-rays by the blood vessel filled with the contrast agent. The intensity feature values may be determined indirectly from the gray values of an angiography image. The intensity (based) features may include, for example, the sum, the distribution or the energy of the gray values within one or more regions in the blood vessel.

A value (e.g., a numerical value) may be determined from the extracted features by any kind of combination among each other. The combination may be a type of regression or classification. The determined value represents a complexity value of the stenosis or a value indicating the possibility of reconstructing the stenosis and/or the blood vessel on the basis of the evaluated images/pictures. The regression may be a manually selected combination of features like the quotient of a local gray value sum and a vessel radius.

Another version of the calculation of the complexity value includes a direct classification based on the extracted features. The result, for example, is a decision of whether further pictures are to be taken or not. Further examples of classification are: a) Stenosis is complex: yes/no or b) diagnostic value is reliable: yes/no. In a simple case, a threshold decision may be performed in addition to the regression or classification. If the resultant value lies above the threshold, taking a further picture is suggested. Otherwise, the stenosis is considered to be sufficiently described by the present pictures.

If picture data is available, for which the complexity value has already been determined in advance (e.g., because the 3D-blood-vessel-model is already known), the data may be used as training data. Regressions based on machine learning that learn the weights of the individual features automatically using the training data are possible. The training data may also be generated by synthetically generated blood vessel models.

The regression may be replaced by a classifier that is directly trained with the aid of the training data. An automated system that may decide whether further images are to be taken or not using the segmented 2D-angiography data is formed.

Figure 6:
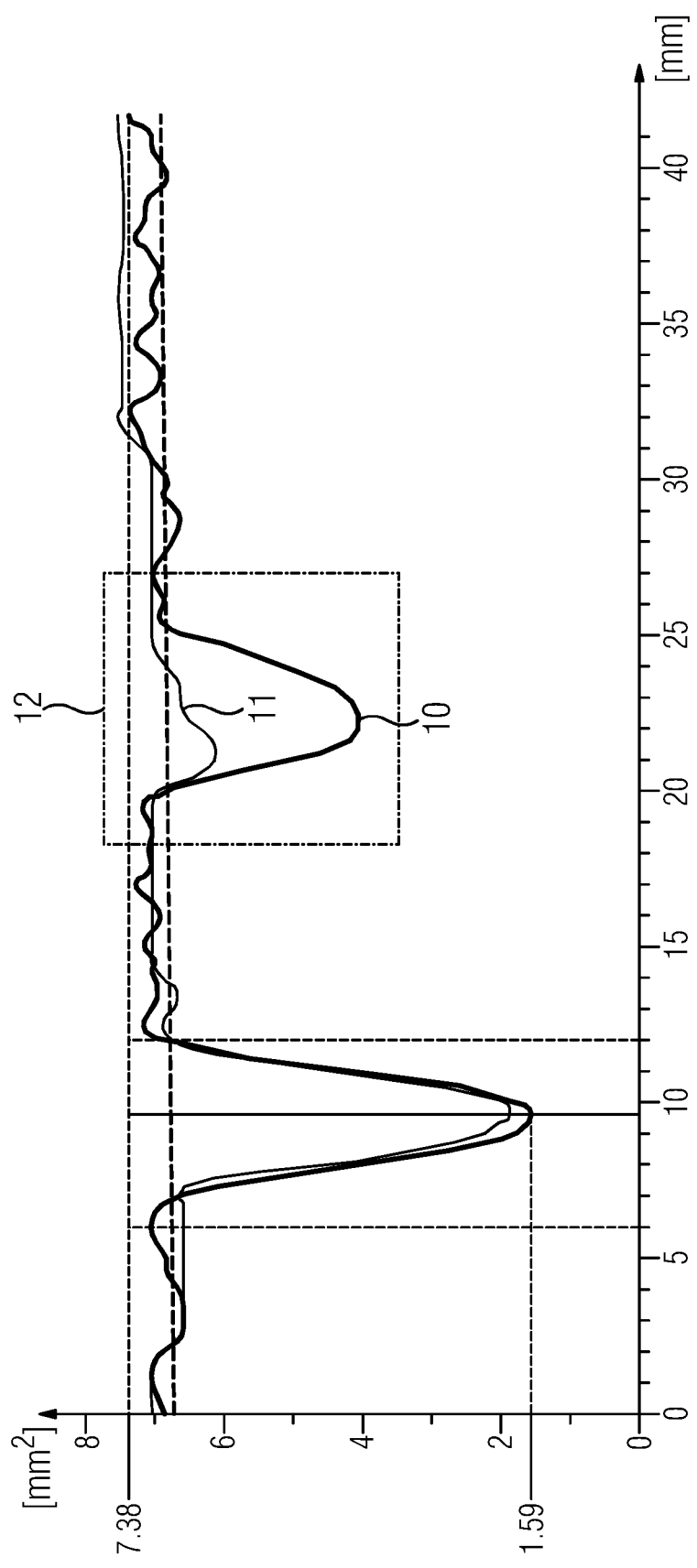
FIG. 6 depicts a measurement of a cross-sectional area of a stenosis based on geometrical data and intensity data according to an embodiment.

FIG. 6 depicts an example where a phantom emulates a blood vessel with an axisymmetric stenosis 1 and an eccentric stenosis 2 like that of FIGS. 1 to 4. A 2D quantitative coronary analysis (QCA) is performed. The cross-sectional area of the blood vessel is measured as geometrical feature along the center line. As intensity feature, a value representing the area is extracted based on the gray values within the vessel segmentation. A segmentation of the 2D-QCA may provide the contour of the stenosis and/or blood vessel. As in FIG. 4 (LAO=0°), where the eccentric stenosis 2 is hidden by the blood vessel 3, the symmetrical stenosis 1 may be clearly identified by its contour. In contrast, the eccentric stenosis 2 just minimally contributes to a modification of the contour of the blood vessel.

The estimated or calculated cross-sectional areas of the 2D-QCA are depicted in FIG. 6. Curve 10 depicts the cross-sectional area determined by intensity feature values, and curve 11 shows the cross-sectional area of the blood vessel determined by geometrical feature values. The cross-sectional area of the symmetrical stenosis is the same when determined as a function of the geometrical feature values or the intensity feature values. The cross-sectional area is not the same for the eccentric stenosis that is marked by rectangle 12 in FIG. 6. The estimated cross-sectional area calculated with the geometrical data has only a small drop in case of the eccentric stenosis 2, whereas the measurement of the area based on the intensity data depicts the eccentric stenosis 2.

A division of the areas obtained from geometrical data or intensity based data may be used as measure for the reconstructability or complexity of the blood vessel, including the stenosis. The result will lead to a greater drop only for the eccentric stenosis 2 that results in a worse reconstructability. Further images might be necessary.

The complexity value may be used for a plurality of applications. The complexity value of the stenosis may be used for judging whether further angiographical images are to be taken. Furthermore, the complexity value of the stenosis may also be used as measure for the reliability of quantities obtained by angiography. Plural such quantities may be determined from angiographical image data for diagnostic purposes.

If it is possible to judge by the complexity value whether the blood vessel is symmetrical, further images may be saved. For example, when the complexity value indicates a circular vessel and a foreshortening-free acquisition of the vessel may be assumed, only a single view may be sufficient for 3D reconstruction. Moreover, the complexity value may be used as feature for manual or automatic classification, for example, in a diagnostic system that determines whether a stenosis is significant or not.

Embodiments provide a combination of one or more geometrical feature values and one or more intensity feature values for evaluating the complexity and/or reconstructability of stenoses from angiographic scenes. Embodiments provide an automated system for the decision whether further images are necessary or not.

Embodiments allow for rapidly judging the reconstructability and/or complexity of a stenosis as a function of already present angiography data. The 3D-reconstruction of complex stenoses may be performed with a minimum number of angiographic images, saving time and resources during medical interventions and reducing the radiation dose for the patient and the physician.

Furthermore, embodiments may provide for a minimum level of reconstruction precision. More complex types of stenoses may be identified and reconstructed exactly (e.g. by images of additional views). The described automation by machine learning may result in a further automation of the work flow and allow for the combination of a high number of geometrical and intensity-based features or feature values, respectively.

The method may also be implemented in the form of a computer program that implements the method on a controller 6 of an X-ray device when the method is run on the controller 6. Similarly, an electronically readable data carrier (not shown) including electronically readable control information stored thereon may be present, that includes at least one described computer program and is configured in such a way that it carries out the described method when the data carrier is used in the controller 6 of an X-ray device.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method of evaluating a geometrical complexity of a stenosis or a section of a vessel, the method comprising:
   providing at least one image of the stenosis or the section of the vessel;
   identifying at least one geometrical feature value of the stenosis, the section of the vessel, or the stenosis and the section of the vessel from the at least one image;
   determining at least one intensity feature value based on a grey level intensity of the stenosis or the section of the vessel from the at least one image; and
   automatically calculating a complexity value related to the geometrical complexity of the stenosis or the section of the vessel in dependency on the at least one geometrical feature value and the at least one intensity feature value of the stenosis or the section of the vessel.

2. The method of claim 1, wherein the at least one image is provided by angiography.

3. The method of claim 1, wherein the at least one geometrical feature value relates to a 2D-contour, a centerline of a blood vessel, or a curvature of the blood vessel.

4. The method of claim 1, wherein the at least one intensity feature value results from an attenuation or excitation of radiation and relates to a sum, a distribution, or an energy of grey values within one or more regions of a blood vessel.

5. The method of claim 1, wherein the complexity value is calculated by regression or classification of the at least one geometrical feature value and the at least one intensity feature value.

6. The method of claim 1, further comprising determining at least three feature values of one or more geometrical features and one or more intensity features,
   wherein automatically calculating the complexity value comprises weighting the at least three feature values.

7. The method of claim 1, wherein a ratio of the at least one geometrical feature value and the at least one intensity feature value is used for calculating the complexity value.

8. The method of claim 1, wherein calculating the complexity value comprises using machine learning.

9. The method of claim 1, wherein the stenosis is an eccentric stenosis.

10. The method of claim 1, further comprising:
    determining whether a 3D-reconstruction of the stenosis or the section of the vessel is possible as a function of the complexity value.

11. The method of claim 1, further comprising:
    determining whether to provide a further image of the stenosis or the section of the vessel as a function of the complexity value.

12. The method of claim 2, wherein the at least one geometrical feature value relates to a 2D-contour, a centerline of a blood vessel, or a curvature of the blood vessel.

13. The method of claim 2, wherein the at least one intensity feature value results from an attenuation or excitation of radiation and relates to a sum, a distribution, or an energy of grey values within one or more regions of a blood vessel.

14. The method of claim 2, wherein the complexity value is calculated by regression or classification of the at least one geometrical feature value and the at least one intensity feature value.

15. The method of claim 2, further comprising determining at least three feature values of one or more geometrical features and one or more intensity features,
wherein calculating the complexity value comprises weighting the feature values.

16. The method of claim 2, wherein a ratio of the at least one geometrical feature value and the at least one intensity feature value is used for calculating the complexity value.

17. The method of claim 2, wherein calculating the complexity value comprises using machine learning.

18. The method of claim 2, wherein the stenosis is an eccentric stenosis.

19. A device for evaluating a geometrical complexity of a stenosis or a section of the vessel, the device comprising:
a memory configured to store at least one image of the stenosis or the section of the vessel;
an analyzer configured to identify at least one geometrical feature value of the stenosis, the section of the vessel, or the stenosis and the section of the vessel from the at least one image, the analyzer further configured to determine at least one intensity feature value based on a grey level intensity of the stenosis or the section of the vessel from the at least one image; and
a processor configured to automatically calculate a complexity value related to the geometrical complexity of the stenosis or the section of the vessel in dependency on the at least one geometrical feature value and the at least one intensity feature value of the stenosis or the section of the vessel.

20. The device of claim 19 wherein the device is used in an angiography system.

* * * * *